United States Patent [19]

Spaeth

[11] Patent Number: 5,209,741
[45] Date of Patent: May 11, 1993

[54] SURGICAL ACCESS DEVICE HAVING VARIABLE POST-INSERTION CROSS-SECTIONAL GEOMETRY

[75] Inventor: Edmund E. Spaeth, Orange, Calif.

[73] Assignee: EndoMedix Corporation, Irvine, Calif.

[21] Appl. No.: 726,496

[22] Filed: Jul. 8, 1991

[51] Int. Cl.⁵ .............................................. A61M 5/00
[52] U.S. Cl. ..................... 604/264; 604/282; 604/280; 604/164
[58] Field of Search ............... 604/283, 282, 281, 280, 604/264, 164, 158, 93; 128/658, 657, 566

[56] References Cited

U.S. PATENT DOCUMENTS

| | | | |
|---|---|---|---|
| 4,239,042 | 12/1980 | Asai | 604/282 X |
| 4,287,892 | 9/1981 | Schiff | |
| 4,411,655 | 10/1983 | Schreck | |
| 4,705,501 | 11/1987 | Wigness et al. | 604/283 X |
| 4,795,426 | 1/1989 | Jones | 604/281 X |
| 4,950,257 | 8/1990 | Hibbs et al. | |
| 4,994,048 | 2/1991 | Metzger | 604/283 |
| 5,019,057 | 5/1991 | Truckai | 604/282 |

OTHER PUBLICATIONS

Medina et al, "A New Type of Adjustable Vascular Introducer for Balloon Valvuloplasty: Technical Note" Cardiovasc Intervent Radiol (1989) 12:169-171.
"Guide-wire Technique for Central Vein Cannulation", S. I. Seldinger Br. Med. J. 2(6026): 21-22, Jul. 3, 1976.
Edward M. Druy, A Dilating Introducer-Sheath for the Antegrade Insertion of Ureteral Stents, Dec. 1985, AJR 145:1274-1276.
M. Maynar et al, A New Technique for Introduction of Large Instruments into the Vascular System, Cardiovasc Intervent Radiol (1988) 11:352-353.

Primary Examiner—John J. Wilson
Assistant Examiner—Jeffrey A. Smith
Attorney, Agent, or Firm—Stetina and Brunda

[57] ABSTRACT

Surgical access devices are provided having axially stiff but radially deformable tubular members for insertion into body cavities, organs or blood vessels. The tubular members include inlet sleeves at their proximal ends for facilitating the introduction of surgical throughput devices. The tubular member is axially stiff to permit non-buckling rotation when it is inserted into the patient's body, and is radially deformable, with a substantially constant circumference, so that it conforms to the outer surface configuration of the inserted throughput devices. This minimizes the size of the insertion opening through which the access devices extend and thereby reduces trauma to the patient when the devices are introduced and used.

15 Claims, 1 Drawing Sheet

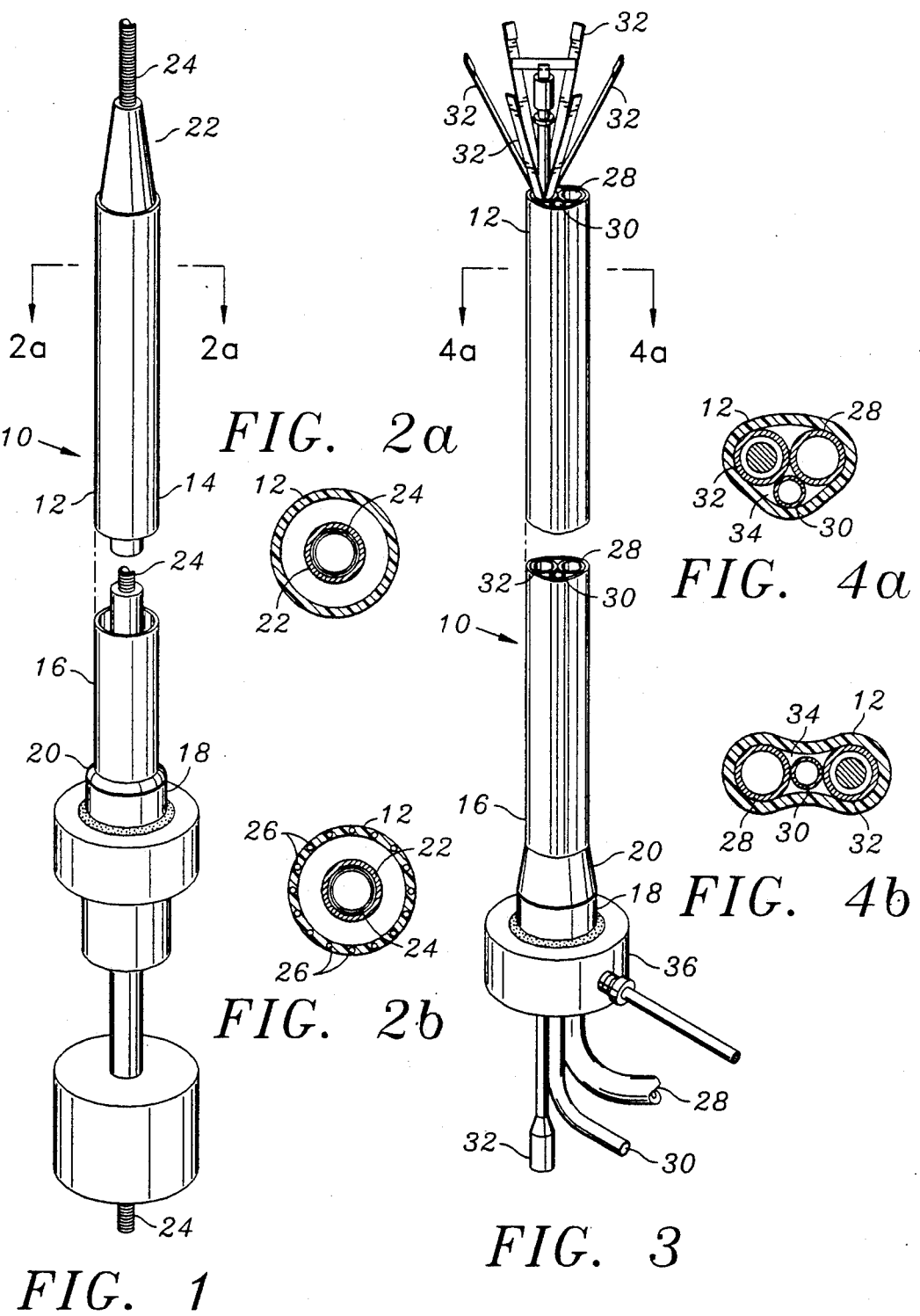

SURGICAL ACCESS DEVICE HAVING VARIABLE POST-INSERTION CROSS-SECTIONAL GEOMETRY

FIELD OF THE INVENTION

The present invention relates generally to medical or surgical instruments which are inserted through the skin into a blood vessel or body cavity. More particularly, the present invention relates to a surgical access device for facilitating the introduction of surgical throughput devices into vascular or body compartments wherein the cross-sectional size and configuration of the access device can be optimized following insertion to minimize trauma.

BACKGROUND OF THE INVENTION

Surgical access procedures utilizing relatively large diameter catheters or cannula are well known in the art. Generally, the prior art access devices are formed as thin walled tubular members having a distal end which is inserted through the skin of the patient and a proximal or extracorporeal end which remains outside the patient's body and is configured to receive a variety of devices including valves, seal structures, additional catheters and surgical throughput devices for performing specific procedures at the distal end of the access device.

The traditional access procedure for positioning these relatively large diameter access devices is the guidewire technique of S. I. Seldinger as described in BR. J. 2(6026): 21–22,#3 July 1976. Briefly, to insert the access device an appropriate area on the skin is identified and prepared for percutaneous puncture then a small diameter needle of sufficient length is introduced through the skin and underlying tissue into the target. A thin, flexible guide wire is inserted through the needle into the target cavity or blood vessel after which the small bore needle is withdrawn over the guide wire leaving the guide wire in the cavity. Using the wire as a guide tapered dilators or progressively larger dilators can be introduced through the outer tissues of the patient until an access channel having the desired diametric size is achieved. The last dilator serves as a guide for the final element of surgical access, a relatively large diameter access tube or introducer. Typically, an assembly of the tubular introducer with a cylindrical dilator extending through the lumen or bore of the introducer is slipped over the guide wire and manipulated into position within the target internal body cavity or blood vessel. After final placement the dilator and the guide wire are removed leaving the access device in position to receive and guide various surgical throughput devices and catheters through the access device into the target area for surgical operation.

To facilitate the manipulation and placement of traditional surgical access devices the devices are provided with a circular cross-sectional configuration. As a result, it is possible to introduce the circular cross section dilators and access tubes into and through tissue by sliding the assemblies over a cylindrical needle or guide wire which allows rotation of the device during the insertion procedure. Rotation about the guide wire axis reduces longitudinal friction as the assembly is pushed through tissue during its introduction. This ability to rotate the round cross section dilator or introducer access device assemblies of the prior art, coupled with their relative rigidity allows the implanting specialist to effectively guide the devices around and through internal organs and other structures to position the working end of the introducer within the target site.

Following removal of the circular dilator the large diameter tubular introducer allows the surgical operator to conduct the desired surgical procedure utilizing a variety of channels and throughput devices which are introduced to the target site through the access device. Because these smaller cannulas, channels and throughput devices vary in number and size depending on the surgical procedure performed, the general tendency has been to combine several channels into a catheter of circular cross section which easily slides through the circular cross section of the introducer. For example, fiber optic bundles, surgical cutting devices, guide wires and cylindrical catheters for aspiration of cut tissue fragments can be put through the access devices to perform sophisticated internal surgical procedures with relatively minor trauma to the patient's skin, musculature and other surrounding tissue.

Early attempts at further reducing the trauma associated with prior art access devices relied upon thin wall construction utilizing elastomeric materials. However, access devices formed of these materials possessed a tendency to buckle or fold during insertion. More recently, an adjustable vascular introducer. for balloon valvulopasty was reported in Cardiovasc. Intervent. Radiol. (1989) 2:169–171 formed of a rolled up plastic sheet in tube form surrounded by a coaxial elastic sheath. This device would expand around the oversized portion of a balloon catheter as it passed through the device. Though apparently successful at overcoming the problems of buckling and folding, the construction of this adjustable introducer provided it with an expandable circular cross section of limited applicability beyond balloon valvulopasty.

Moreover, while a circular cross section access device may be preferable for the insertion procedure itself, the resultant circular cross section of the introducer is not always the smallest, least traumatic, or optimum cross-sectional configuration for conducting the subsequent surgical procedure. Depending upon the number and type of throughput devices necessary to perform the intended surgical procedure, an ellipsoidal, figure-eight, triangular, or other non-circular cross section would result in more favorable access and require a smaller, less traumatic dilation diameter.

Accordingly, one of the objects of the present invention is to provide a surgical access device or introducer having optimized cross-sectional geometry for both insertion of the device and for post-insertion surgical procedures.

It is an additional object of the present invention to provide an access device having a variable cross section which, following insertion of the device, can be modified to an optimized cross-sectional size and shape depending upon the intended surgical procedure to be conducted through the access device.

It is an additional object of the present invention to provide an access device having a variable cross section which can be manufactured utilizing simple and inexpensive materials and techniques.

SUMMARY OF THE INVENTION

These and other objects are achieved by the surgical access device of the present invention which, in accordance with a broad structural aspect of the invention, includes an axially stiff tubular member having a distal end, a proximal end and a hollow inner lumen extending axially therethrough. The distal end portion of the tubular member is inserted into a body cavity, organ or blood vessel while the proximal end portion remains in an extracorporeal position where one or more surgical throughput devices can be inserted into the proximal end and through the tubular member of the access device to an outlet port at the distal end thereof.

In order to ease the entry and placement of throughput devices within the tubular member the extracorporeal proximal end portion is provided with means for facilitating the introduction of the throughput devices. In an exemplary embodiment the means for facilitating is an enlarged, generally circular or tubular inlet sleeve which flares or steps (preferably in a smooth taper) outwardly in a transitional section from the proximal end portion of the tubular member much like a tubular funnel. Preferably, the inlet sleeve is formed to be relatively rigid in order to maintain its shape and thereby simplify the introduction of the surgical throughput devices.

Unlike prior art access devices, the tubular member of the present invention is also provided with means for optimizing the cross-sectional area and configuration of the tubular member relative to the overall cross-sectional area and configuration of the throughput devices placed within the access device. Additionally, to facilitate the initial placement and insertion of the access device in a body cavity, organ or blood vessel the tubular member can be deformed utilizing circular cross section dilators of appropriate dimensions to provide an easily manipulatable assembly which can be placed in the same manner as traditional surgical access devices. However, because the post-insertion geometry is optimized and typically smaller in area than a circular cross section access device dimensioned according to the prior art the device of the present invention has a smaller insertion circular cross section during placement. Accordingly, tissue trauma is reduced.

Once the cylindrical dilator has been removed and replaced with the surgical throughput devices necessary to perform the intended surgical procedure the tubular member assumes the optimal cross-sectional configuration and area as defined by the throughput devices. Preferably, this variable post-insertion geometry is achieved by forming the tubular member of an axially stiff yet radially deformable material such as a bio-compatible elastomer of appropriate wall thickness. The material also may include longitudinal stiffening elements. Additionally, in an alternative embodiment of the present invention the tubular member is pre-formed with an optimized non-circular cross-sectional configuration as defined by specific throughput devices. By using a dilator with a circular cross section the pre-formed cross section of this alternative embodiment will assume a cylindrical shape facilitating the insertion.

The proximal end of the tubular member also may be provided with connectors or housings for sealingly attaching check valves and other connecting devices to facilitate the subsequent surgical procedures conducted through the access device.

Other features and advantages of the present invention will become apparent from the following detail description, taken in conjunction with the accompanying drawings which illustrate, by way of example, the principles of the present invention.

BRIEF DESCRIPTION OF THE DRAWINGS

FIG. 1 is an elevational view of an access device with a section removed illustrating the principles of the present invention in conjunction with a tapered cylindrical dilator.

FIG. 2a is a cross-sectional, plan end view taken through the line 2a—2a of FIG. 1.

FIG. 2b is a cross-sectional view illustrating the construction of an alternative embodiment of the present invention taken through the plane 2a—2a of FIG. 1.

FIG. 3 is an elevational view of the access device of the present invention shown with a section removed and accommodating several exemplary surgical throughput devices.

FIG. 4a is a cross-sectional, plan view taken along the line 4a—4a of FIG. 3 showing the optimized cross-sectional configuration and area of the tubular member relative to the throughput devices.

FIG. 4b is a cross-sectional view taken along the plane 4a—4a of FIG. 3 showing an alternative optimized post-insertion cross-sectional geometry.

DETAILED DESCRIPTION

The access device of the present invention is designed for use in conjunction with surgical procedures requiring access to internal body cavities, organs or blood vessels. The access device is designed to minimize trauma to surrounding tissue during its placement and during the subsequent surgical procedure, and to prevent leakage of bodily fluids while providing improved administration and control of the surgical instruments utilized. In addition to providing optimized minimal cross-sectional areas and configurations during and following insertion, the access device of the present invention is simple and inexpensive to manufacture and can be inserted into position utilizing conventional dilation and guide wire techniques.

Referring more particularly to the drawings, FIGS. 1, 2a and 2b illustrate an embodiment of the access device of the present invention, generally indicated by reference 10, in its pre-insertion configuration. Access device 10 is provided with an axially stiff tubular member 12 formed of a thin wall radially deformable material and having a distal end portion 14 for insertion into a target body cavity, organ or blood vessel and a proximal end portion 16 for positioning in an extracorporeal location outside of the tissue surrounding the access site. As those skilled in the art will appreciate, the overall length and relative dimensions of device 10 are determined by the depth of penetration needed to perform the surgical procedure intended as well as by the associated dimensions of the surgical throughput devices necessary to conduct the operation. As such, the access device shown in FIG. 1 is exemplary only and is not intended to limit the present invention to specific relative dimensions.

However, it is anticipated as being within the scope of the present invention to produce access devices ranging in length from approximately 50 mm to 500 mm with diameters ranging from approximately 1 mm to 20 mm. Though these dimensions are exemplary only and larger or smaller size access devices are within the scope of the present invention it is believed that these exemplary dimensions are suitable for most currently known surgical procedures utilizing access devices such as those of the present invention.

Access device 10 also includes means for facilitating the introduction of the throughput surgical devices into extracorporeal proximal end portion 16 of tubular member 12. In the exemplary embodiment of FIG. 1 this means for facilitating is illustrated as an enlarged, generally circular inlet sleeve 18 projecting from the extracorporeal proximal end 16 of the tubular member 12. Preferably, inlet sleeve 18 has a generally cylindrical or tubular construction with an enlarged diameter relative to the average cross-sectional diameter of the tubular member 12. For example, an exemplary diameter approximately 30% larger than the diameter of tubular member 12 is preferred as this greatly simplifies the introduction of single or multiple surgical throughput devices into proximal end portion 16. However, inlet sleeve diameters ranging from approximately 20% to 50% larger than the average diameter of tubular member 12 are also contemplated as being within the scope of the present invention.

In addition to being dimensioned to easily receive the introduction of surgical throughput devices, inlet sleeve 18 is preferably formed of a relatively stiff but resilient wall material to provide it with the capability to substantially resist deformation but still assist the manipulation and introduction of surgical throughput devices into access device 10. However, it should be appreciated that inlet sleeve 18 may also be formed of a resilient, flexible material within the scope of the present invention.

As shown in FIG. 1 the enlarged diameter of the inlet sleeve 18 steps down to the diameter of proximal end portion 16 over the axial extent of a generally tubular transitional section 20 disposed in communication between inlet sleeve 18 and proximal end 16. This radially deformable transitional section serves to direct the passage of surgical throughput devices (not shown) along the axial lumen within tubular member 12. It is preferred that transitional section 20 be formed of an axially stiff material in order to allow it to accommodate the surgical throughput devices without buckling along the axial extent of access device 10. More importantly, this construction allows the surgical throughput devices to deform tubular member 12 to an optimized cross-sectional configuration as discussed in detail below.

Further illustrating the principles of the present invention, access device 10 is shown in FIGS. 1, 2a and 2b positioned upon a cylindrical circular dilator 22, which in turn is positioned over a guide wire 24. In this configuration access device 10 is provided with a generally circular cross-sectional configuration as shown in FIG. 2a. This enables the access device/dilator assembly to be inserted into a patient's body using traditional guide wire insertion techniques. Additionally, the concentric circular cross section provided by dilator 22 enables the access device/dilator assembly to be rotated about guide wire 24 during insertion and placement of the access device in order to reduce frictional drag along the longitudinal extent of access device 10 and, as a result, to reduce tissue trauma during placement of the device. The tapered tip of cylindrical circular dilator 22 gradually opens the surrounding tissue and also minimizes trauma during placement.

Additionally, it should be emphasized that tissue trauma during placement of access device 10 is further reduced as the result of the device having an optimized, minimal cross-sectional geometry. More specifically, because prior art access devices having circular cross-sectional post-insertion geometry typically have a diameter equal to the sum of the diameters of the throughput devices, their fixed insertional diameter is significantly larger than that provided by the access device of the present invention. It also should be noted, that smaller optimized diameters reduce the size of the tract the introducer leaves in the tissue after removal of the introducer. The smaller tract reduces leakage of bodily fluids and heals faster than a larger tract. Because access device 10 is provided with a variable post-insertion cross-sectional geometry its insertion diameter can be reduced to that minimally necessary to provide a sufficient circumferential dimension to encompass the optimized, generally non-circular post-insertion geometry as will be discussed in detail with respect to FIGS. 4a and b.

As noted above, following insertion of distal end portion 14 of tubular member 12 into a target body cavity, organ or blood vessel the overall cross-sectional area and cross-sectional configuration of tubular member 12 is variable to an optimized configuration. Thus, access device 10 includes means for optimizing the cross-sectional area and configuration of tubular member 12. Preferably, the means for optimizing will comprise an axially stiff, radially deformable wall material forming tubular member 12. Exemplary deformable wall materials include a variety of bio-compatible semi-rigid elastomers such as silicone, polyvinylchloride, polyethylene, teflon and nylon. As those skilled in the art will appreciate, depending upon the resiliency of the wall material utilized the wall thickness should be sufficient to resist axial deformation and buckling during insertion of access device 10 yet sufficiently deformable to allow the cross-sectional area and configuration of tubular member 12 to be optimized to the minimal cross-sectional area and configuration needed to conduct the subsequent surgical throughput procedure. Exemplary wall thickness range from approximately 0.003 to 0.012 inch.

As shown in FIG. 2b, an alternative embodiment of the means for optimizing the cross-sectional area and configuration of the present invention is formed of a flexible wall material defining tubular member 12 and further incorporating longitudinal stiffening elements 26. For example, the wall material of tubular member 12 can be formed of extruded nylon and other elastomers and stiffening elements 26 can be formed of compatable semi-rigid elastomers or extruded mechanical elements. In this manner, tubular member 12 can be provided with a relatively thin wall thickness while retaining the desired axial rigidity and radial deformability.

Turning now to FIG. 3, an alternative embodiment of the access device 10 of the present invention is illustrated in its post-insertion configuration relative to a number of throughput devices. Initially, an interesting feature of this embodiment of FIG. 3 is tubular transitional section 20 which, in this alternative embodiment, is illustrated as a generally tubular section coaxially disposed in communication between inlet sleeve 18 and extracorporeal proximal end 16 and provided with a generally smoothly tapered or conical circular cross section along its axial extent (as opposed to the step-like transitional section shown in the embodiment of FIG. 1). This smoothly tapered transitional section 20 is formed of a radially deformable axially stiff material like the remainder of tubular member 12 as this assists in the introduction and guidance of surgical throughput devices into and through access device 10.

Also shown in FIG. 3 are a variety of surgical throughput instruments which serve to illustrate the features of the present invention. More particularly, an aspiration catheter 28, guide wire 30, and rotary lithotrite 32 are shown as would be utilized for the removal of gallstones. Those skilled in the art will appreciate that catheter 28, guide wire 30 and lithotrite 32 are exemplary only and do not limit the scope of the present invention. Accordingly, a wide variety of surgical throughput devices can be utilized in connection with the present invention.

More importantly, as shown in FIGS. 4a and 4b the cross-sectional geometry of access device 10 is variable from that of the traditional circular pre-insertion configuration of FIGS. 2a and 2b to the optimized cross-sectional configurations and areas of post-insertion FIGS. 4a and 4b. More specifically, FIGS. 4a and 4b illustrate alternative optimized post-insertion cross-sectional geometries of tubular member 12 relative to the overall cross-sectional area and cross-sectional configuration of throughput devices 28, 30 and 32. The non-circular cross-sectional configurations illustrated in FIGS. 4a and 4b present the minimal cross section necessary to access the target surgical site with throughput devices 28, 30 and 32 and thus minimize trauma to the tissue surrounding access device 10 during the surgical procedure. Moreover, unlike conventional rigid access devices or those which expand to accommodate bulky surgical instruments such as balloon catheters, the access device of the present invention minimizes the cross-sectional geometry relative to the surgical throughput devices.

It should also be noted that, as shown in FIG. 4b, the lumen 34 within tubular member 12 automatically forms an additional conducting channel between throughput devices 28, 30 and 32. As a result, continuous irrigation can be accomplished through access device 10 without the need for an additional throughput catheter.

Of equal importance, following insertion of access device 10 and the introduction of one or more throughput devices into tubular member 12 additional throughput devices can be inserted into access device 10 and the cross-sectional area and configuration will automatically accommodate to the optimum size and shape. Thus, variations in surgical procedure can be accomplished utilizing the access device of the present invention which could not be achieved with prior art devices of similar size.

It should also be noted that it is contemplated as being within the scope of the present invention to manufacture tubular member 12 in the final desired post-insertion cross-sectional shape and configuration. Depending upon the intended surgical procedure and the associated surgical throughput devices which determine the optimum cross-sectional area and configuration, this cross section can be shaped as the triangular ellipsoidal of FIG. 4a, the figure-eight of FIG. 4b, an oval, egg-shape or any other generally non-circular cross-sectional shape of the appropriate size. Because of the radially deformable nature of the wall material forming tubular member 12 this precast optimum configuration will deform to a relatively small, generally circular configuration when cylindrical circular dilator 22 is positioned within access device 10 for the surgical insertion procedure. When dilator 22 is removed following insertion the tubular member 12 regains its original optimized shape to accommodate the throughput devices.

In this alternative embodiment of the means for optimizing the cross-sectional area and cross-sectional configuration of tubular member 12, the optimum cross-sectional configuration can be achieved through casting or extruding tubular member 12, or at least distal end portion 14 thereof, in the desired shape to accommodate the desired throughput devices. Extrusion and subsequent heat forming as known in the art also may be utilized to form either embodiment of the present invention.

As shown in FIG. 3, inlet sleeve 18 provides a tapered entry section for the introduction of throughput devices 28, 30 and 32. Additionally, access device 10 can be provided with various means for sealingly engaging an attachment or housing 36 adjacent to proximal end portion 16 of tubular member 12. Preferably, housing 36 will be sealingly attached to inlet sleeve 18 by bonding. However, other means for sealingly engaging adapters or housings to the tubular member such as 0-ring seals, fused junctions and the like are also contemplated as being within the scope of the present invention. In this manner, housing 36 provides for convenient sealing connection to a variety of surgical implements outside of the body.

In closing it is to be understood that the embodiments of the invention disclosed herein are illustrative of the principals of the invention. Other modifications may be employed which are within the scope of the invention; thus, by way of example but not of limitation, alternative cross-sectional configurations may be precast into the tubular member other than those generally shown and alternative materials and wall thickness may be utilized to form the tubular member. Additionally, an expandable balloon may be provided adjacent to the distal end of the tubular member connected to an air channel passing through the wall of the tubular member to seal and retain the access device in position following its placement. Accordingly, the present invention is not limited to that precisely as shown and described in the present specification.

What is claimed is:

1. A surgical access device comprising:
   a tubular member having a distal end portion for insertion through an insertion opening into a body cavity, organ or blood vessel and an extracorporeal proximal end portion for the introduction of at least one throughput device into said tubular member; and
   means for facilitating the introduction of the at least one throughput device into said extracorporeal proximal and portion of said tubular member;
   said tubular member being formed of flexible wall material forming said tubular member and having longitudinal stiffening elements incorporated therein to permit non-buckling rotation of the tubular member when it is inserted into the body cavity, organ or blood vessel, and said tubular member being radially deformable, with a substantially constant circumference, to permit the tubular member to optimize cross-sectional area of the insertion opening by conforming to the outer surface configuration of at least one throughput device introduced into said tubular member;
   whereby tissue trauma is reduced at the insertion opening by reducing the size of the opening.

2. The surgical access device of claim 1 wherein said wall material defines a pre-formed optimized cross-sectional area and cross-sectional configuration which can be deformed to a generally circular cross-sectional configuration to facilitate the insertion of said tubular member into a body cavity, organ or blood vessel.

3. The surgical access device of claim 1 wherein said means for facilitating the introduction of the at least one throughput device comprises:
an enlarged, generally circular inlet sleeve projecting from said extracorporeal proximal end of said tubular member and adapted to receive and guide the at least one throughput device into said tubular member.

4. The surgical access device of claim 3 further comprising a generally tubular transitional extending axially and section coaxially disposed in communication between said inlet sleeve and said extracorporeal proximal end portion of said tubular member.

5. The surgical access device of claim 4, wherein said tubular transitional section is smoothly tapered as the section extends axially and is formed of a radially deformable, axially stiff material.

6. The surgical access device of claim 1 further comprising means for sealingly engaging a housinq adjacent to said extracorporeal proximal end portion of said tubular member.

7. A surgical access device comprising:
a tubular member having a distal end portion for insertion through an insertion opening into a body cavity, organ or blood vessel and an extracorporeal proximal end portion for the introduction of at least one throughput device into said tubular member;
an enlarged, generally circular inlet sleeve projecting from said extracorporeal proximal end portion of said tubular member to facilitate the introduction of the at least one throughput device into said tubular member;
said tubular member being axially stiff, to permit smooth, non-buckling rotation of the tubular member when it is inserted into the body cavity, organ or blood vessel, and radially deformable, with a substantially constant circumference, to permit the tubular member to optimize the cross-sectional area of the insertion opening by conforming to the outer surface configuration
whereby tissue trauma is reduced at the insertion opening by reducing the size of the opening.

8. The surgical access device of claim 7 wherein said tubular member comprises:
a flexible wall material forming said tubular member and further incorporating longitudinal stiffening elements.

9. The surgical access device of claim 7 wherein said tubular member defines a pre-formed optimized cross-sectional area and cross-sectional configuration which can be deformed to a generally circular cross-sectional configuration to facilitate the insertion of said tubular member into a body cavity, organ or blood vessel.

10. The surgical access device of claim 7 further comprising a generally tubular transitional section extending axially and coaxially disposed in communication between said inlet sleeve and said extracorporeal proximal end portion of said tubular member.

11. The surgical access device of claim 10, wherein said tubular transitional section is smoothly tapered as the section extends axially and is formed of a radially deformable, axially stiff material.

12. The surgical access device of claim 7 further comprising means for connecting a housing in sealing engagement with said inlet sleeve.

13. A surgical access device having optimizable post-insertion geometry, said device comprising:
a generally tubular member formed of a radially deformable, axially stiff material and having a distal end portion for insertion into a body cavity, organ or blood vessel and an extracorporeal proximal end portion for the introduction of at least one throughput device;
an enlarged, generally circular inlet sleeve projecting from said extracorporeal proximal end portion to facilitate the introduction of the at least one throughput device into said tubular member;
said tubular member being axially stiff, to permit smooth, non-buckling rotation of the tubular member when it is inserted into the body cavity, organ or blood vessel, and radially deformable, with a substantially constant circumference, to permit the tubular member to optimize the cross-sectional area of the insertion opening by conforming to the outer surface configuration;
whereby tissue trauma is reduced at the insertion opening by reducing the size of the opening.

14. The surgical access device of claim 13 further comprising:
means for connecting a housing in sealing engagement with said inlet sleeve.

15. The surgical access device of claim 13 wherein said tubular member is provided with a pre-formed optimized cross-sectional area and an optimized non-circular cross-sectional configuration which can be deformed to a generally circular cross-sectional configuration to facilitate the insertion of said tubular member into a body cavity, organ or blood vessel.

* * * * *

UNITED STATES PATENT AND TRADEMARK OFFICE
CERTIFICATE OF CORRECTION

PATENT NO. : 5,209,741
DATED : May 11, 1993
INVENTOR(S) : Edmund E. Spaeth

It is certified that error appears in the above-indentified patent and that said Letters Patent is hereby corrected as shown below:

Column 1, line 31, after BR., insert --Med.--.
Column 2, line 27, delete the period (.) after "introducer" and before "balloon".
Column 2, line 29, delete "2" and substitute therefore --12--.
Column 4, line 7, after "view" and before "taken", insert --thereof--.
Column 4, line 16, after "plan" and before "view", insert --end--.
Column 8, line 51, delete "and" and substitute therefore --end--.
Column 9, line 13, after "tubular transitional section" insert "extending axially and".
Column 9, line 45, after "configuaration", insert --of the at least one throughput device introduced into said tubular member;--.

Signed and Sealed this

Twenty-second Day of February, 1994

Attest:

BRUCE LEHMAN

*Attesting Officer*  *Commissioner of Patents and Trademarks*